United States Patent [19]

Barnick

[11] Patent Number: 5,232,383
[45] Date of Patent: Aug. 3, 1993

[54] MEDICAL SNAP CONNECTOR

[76] Inventor: Robert C. Barnick, 2300 40th Ave. NE., Minneapolis, Minn. 55421

[21] Appl. No.: 964,543

[22] Filed: Oct. 21, 1992

[51] Int. Cl.⁵ .............................................. H01R 4/48
[52] U.S. Cl. .................................... 439/859; 128/641
[58] Field of Search ............... 439/500, 818, 848, 856, 439/857, 859; 128/639, 641, 802

[56] References Cited

U.S. PATENT DOCUMENTS

| | | |
|---|---|---|
| 1,014,718 | 1/1912 | Parsons . |
| 2,448,509 | 9/1948 | Antony, Jr. et al. . |
| 2,916,719 | 12/1959 | Toms . |
| 3,085,577 | 4/1963 | Berman et al. ............ 128/418 |
| 3,155,808 | 11/1964 | Wiley . |
| 3,611,255 | 10/1971 | Shroyer . |
| 3,750,094 | 7/1973 | Zenkich . |
| 4,094,571 | 6/1978 | Benjamin . |
| 4,112,941 | 9/1978 | Larimore . |
| 4,155,614 | 5/1979 | Hall . |
| 4,331,153 | 5/1982 | Healy ....................... 128/641 |
| 4,460,231 | 7/1984 | Muz . |
| 4,490,005 | 12/1984 | Hovey ...................... 128/641 |
| 4,635,642 | 1/1987 | Cartmell et al. ............ 128/641 |
| 4,671,591 | 6/1987 | Archer ...................... 439/346 |
| 4,699,679 | 10/1987 | Cartmell et al. ............ 128/641 |
| 4,734,064 | 3/1988 | Knapp et al. .............. 439/856 |
| 4,757,817 | 7/1988 | Healy ....................... 128/641 |
| 5,088,942 | 2/1992 | Welsh et al. ............... 439/856 |

FOREIGN PATENT DOCUMENTS 2538174 6/1984 France .................. 439/859

Primary Examiner—P. W. Echols
Attorney, Agent, or Firm—Haugen and Nikolai

[57] ABSTRACT

An electrical medical connector having an integrally formed conductive pad including several flexible fingers defined by several radial slots. Each contact finger is flexible radially outward into a conforming recess when a male conductive stud from a contact pad is inserted within the connector. Each flexible finger engages a narrowed portion of the male stud to form a conductive path at a first contact region, wherein a surface of each contact finger engages collar portion of the male stud to provide a second contact region. Due to the redundancy of the first and second contact regions, damage, loss or wear of one contact finger does not result in degraded electrical contact between the connector and the stud, hence, a more reliable connector is established. The conductive pad formed in insulating connector body includes an integrally formed crimp finger which is crimped to a conducting wire. The connecting wire typically is routed to a medical device such as an electrocardiograph. Because the crimp finger is integrally formed with the conductive pad, time-consuming soldering or welding between the two is avoided to provide an improved and more reliable physical and electrical connection. The radial fingers which are biased toward the received male stud provide an increased bite against the male stud in contrast to two tangent contacting surfaces to reduce the effects of worn or dirty surface areas.

8 Claims, 2 Drawing Sheets

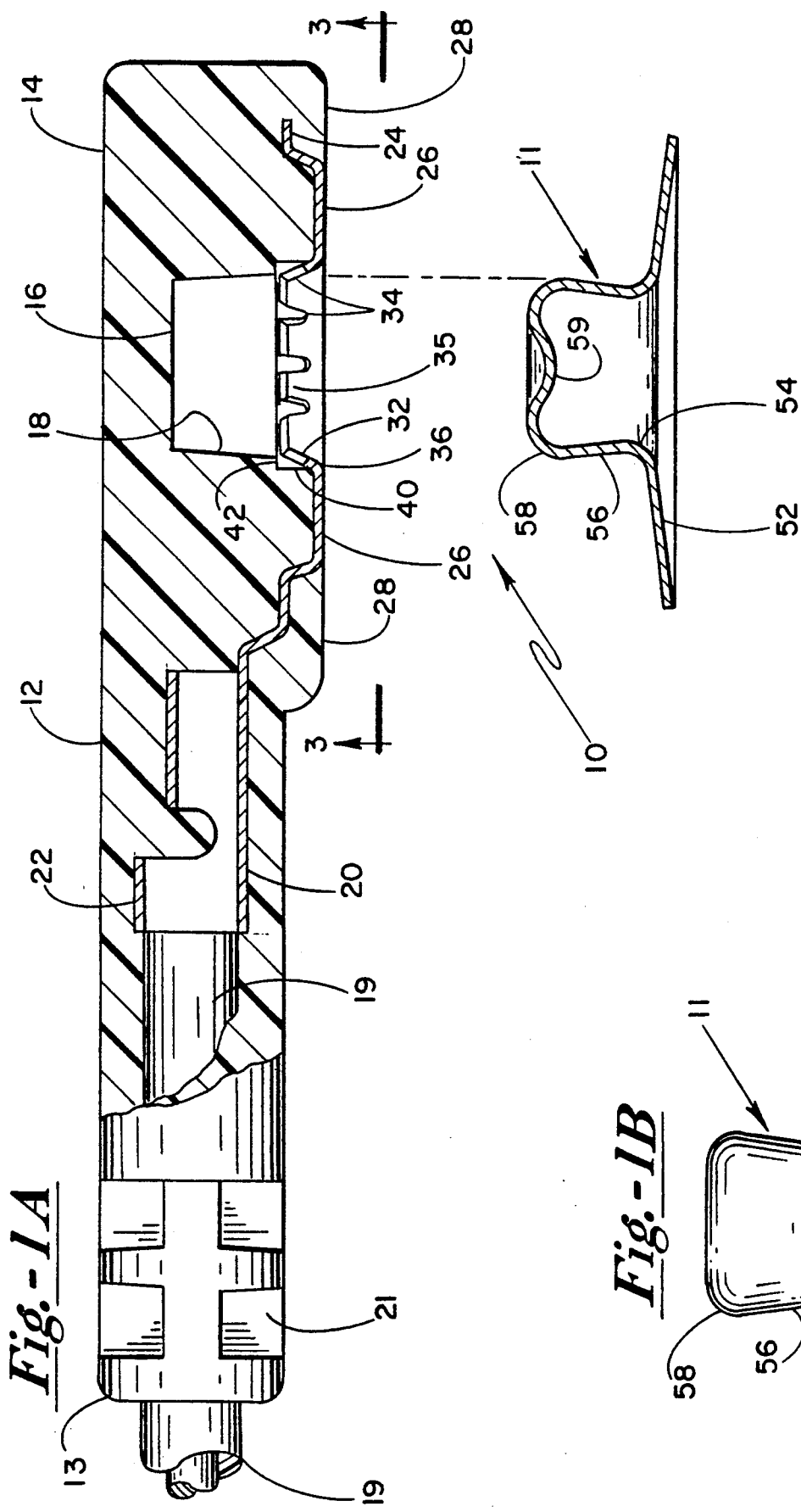

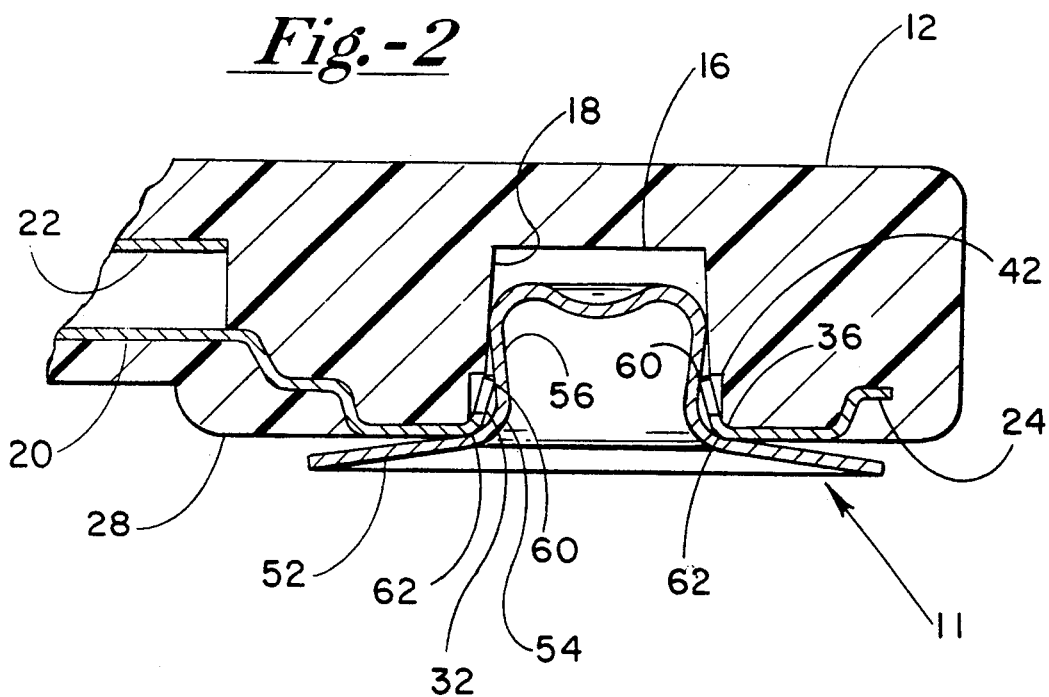
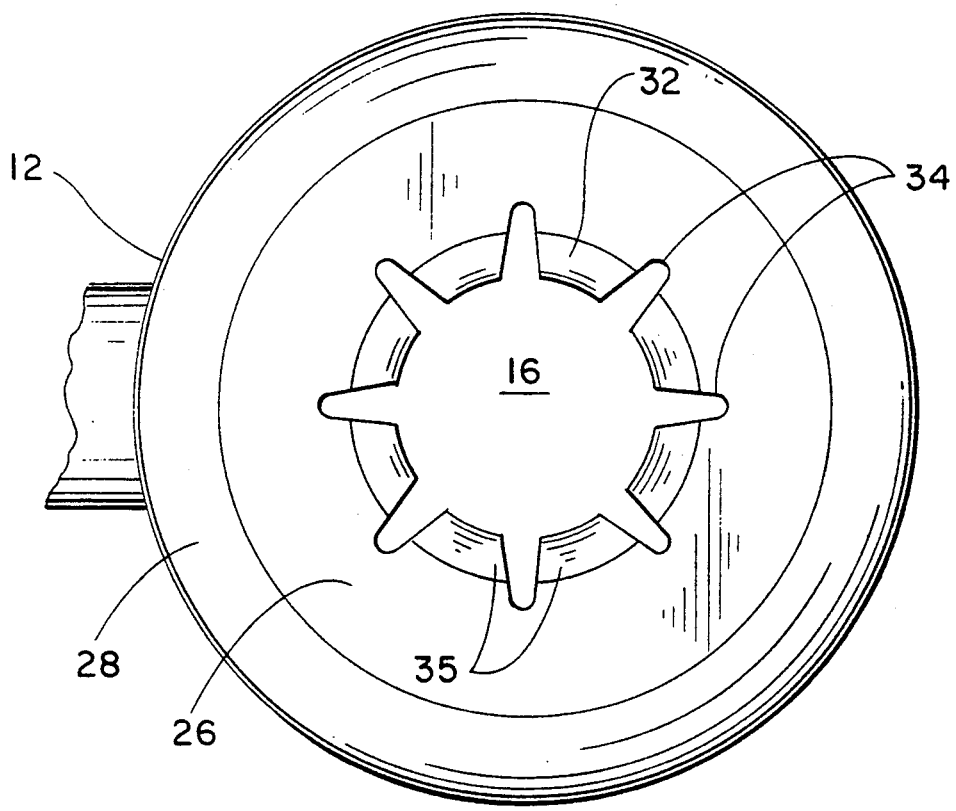

MEDICAL SNAP CONNECTOR

BACKGROUND OF THE INVENTION

I. Field of the Invention

This invention relates generally to medical snap connectors which are connectable to ball-stud patient engaging electrodes and, more particularly, to a snap connector having an improved contact area engaging the received male stud.

II. Discussion of the Prior Art

In recent years a variety of medical snap connectors and associated male studs have been introduced into the medical field. Generally, electrodes containing a male terminal, or ball-stud, are adhesively secured to the skin of a patient. The stud is adapted to snap into a female terminal in the connector and is typically shaped in accordance with ANSI standards. A conductive lead wire is connected to the female terminal and completes an electrical path between the male stud and an electromedical device such as an electrocardiograph. The stud portion of the electrode is generally connected to a metallic plate which is, in turn, connected to the patient's skin by means of an electrically conductive material such as an electrolyte gel.

The major drawback associated with various snap connectors is that the quality of a mechanical connection between the female snap connector and the male stud is degraded through extensive usage. Further, these female snap-on connectors are rather complex in design and relatively expensive to manufacture. The conductors are usually manually soldered or welded to the female terminal which is time consuming, occasionally unreliable, and a rather difficult process to automate.

U.S. Pat. No. 4,671,591, issued to Archer, teaches an electrical connector having a retainer spring captured in a cavity and engaging a stud. This connector requires soldering of the spring to the conductor which is time consuming. Further, only one contact region between the conductor and the stud is provided.

U.S. Pat. No. 3,750,094, issued to Zenkich, teaches an electrical connector having a spring compressed in a bore for engaging a narrowed portion of a male stud. The drawback of this connector is that should one of the spring arms fail due to excessive wear, for example, the whole connector is nonfunctional. Further, only one contact region is established between the spring and the stud.

U.S. Pat. No. 4,112,941, issued to Larimore, teaches a snap-on connector with a magnetic element. This connector has only one contact region, and further, teaches a lead wire which is only electrically connected to shell 26.

U.S. Pat. No. 4,460,231, issued to Muz, teaches an electrical connector having a spring element with a longitudinal slit. This connector also has only one contact region.

OBJECTS

It is according a principal object of the present invention to provide an improved medical electrical connector adaptable to a standard conductive ball-stud electrode having a more reliable and adaptable contact area.

A further object of the present invention is to provide a medical connector having an improved design for connecting an integral conductive member to an extending conducting wire.

SUMMARY OF THE INVENTION

The foregoing features and objects are achieved by providing a snap-on connector having a conductive pad with a plurality of fingers engaging a received conductive male stud. A more reliable electrical connection between the conductive pad and the conducing wire is established by providing a conductive pad having an integrally formed crimping finger crimped to the conducting wire to form a good mechanical and electrical connection. The connector comprises a connector body formed of insulating material and shaped to form a socket having an opening and defining a socket wall. A plate-like conductive pad is formed in the insulating body and is coupled to an electrical conductor. The conductive pad has an aperture defining an annular contact region having a rim and a rim surface. The rim surface has several radial slits or notches defining several rim fingers. A portion of the rim is spaced from the socket wall such that upon inserting the stud into the socket, the rim fingers flex radially outward and engage the stud at a first contact area, wherein the rim surface engages a collar of the conductive male stud at a second contact area.

The socket wall formed in the insulating body further includes an annular recess proximate the rim fingers. When the stud is inserted into the socket, the rim fingers radially flex toward the recess to provide clearance for the received male stud. The recess is preferably closely conformed to the flexed rim fingers. The contact region is generally frusto-conical shaped and tapering at least partially into the socket The connector is further defined wherein the conductive pad includes an integral crimp finger crimped to the conductor to form a good mechanical and electrical contact prior to plastic injection molding the connector body thereabout. This crimping feature can be an automated process, and is substantially more reliable and quicker than soldering or welding.

The improved connector provides multiple engagement points at two contact regions ensuring a redundant electrical connection, providing a connector with a longer life cycle. Further, the conductive pad is connected to the insulating wire in a more convenient and reliable manner. The connector is rotatable about the inserted stud and adaptable to sudden and unforeseen movements of a patient. Finally, this more reliable connector can be manufactured relatively inexpensively and quickly.

BRIEF DESCRIPTION OF THE DRAWINGS

Other objects, features and advantages of the present invention will become apparent to those skilled in the art through the description of the preferred embodiment, claims, and drawings herein wherein like numerals refer to like elements.

FIG. 1A is an exploded view of a partial sectional representation of a connector according to the present invention;

FIG. 1B is a simple representation of a compatible conductive male stud insertable into the connector of the present invention;

FIG. 2 is a partial sectional view of the connector according to the present invention receiving a male stud, illustrating the first and second contact regions; and FIG. 3 is a bottom view of the connector illustrating the radial slots defining the several flexible contact fingers.

DESCRIPTION OF THE PREFERRED EMBODIMENT

Referring to FIGS. 1A and 1B, a female connector according to the present invention is illustrated generally at 10. Connector 10 is connectable to a male ball stud 11 and comprises molded plastic connector body 12 having a proximal end 13 and a distal end 14. An integrally formed circular socket 16 defines a circular wall 18 in distal end 14. An insulated conductor 19 is integrally formed in proximal end 13, wherein end 13 has several notches 21 to form a strain relief. Conductor 19 extends to a plate-like conductive pad 20 having an integrally formed semicircular finger 22 located within a midsection of connector body 12. Finger 22 is mechanically crimped to insulated conductor 19 prior to assembly with molded plastic to form a secure mechanical and electrical connection. Plate-like conductive pad 20 is integrally formed in connector body 12 extending from finger 22 to a distal end 24 with an exposed conductive planar pad surface 26 therebetween which is flush with an annular surface 28. Distal end 24 of pad 20 is integrally formed within distal end 14 of connector body 12 for reinforcement and is curved in an S-shaped finger. A circular opening in conductive pad 20 defines a frusto-conical rim 32 concentrically arranged with socket 16. Rim 32 has several radial notches or slits 34 defining several generally trapezoidal fingers 35. Slits 34 permit fingers 35 to be flexed radially outward when an outward lateral force is urged thereupon. Conductive pad 20 has an annular rounded edge 36 encompassing rim 32 defined between surface 26 and rim 32. Edge 36 is curved inward from exposed surface 26 toward socket 16 such that rim 32 tapers generally conically inward toward a bottom of socket 16. An annular recess 40 forming annular shoulder 42 defined in connector body 12 concentrically encompasses socket 16 in a spaced relationship from rim 32 such that rim 32 can flex radially outward within recess 40. Recess 40 closely conforms to a fully radially flexed rim 32.

Conductive stainless steel stud 11 comprises a hollow shell and includes a tapered annular collar 52 leading to a curved distal portion 54. Distal portion 54 leads to an intermediate portion 56 angling approximately 15° off of vertical alignment. Intermediate portion 56 extends to a proximal end 58 having a larger diameter than both intermediate portion 56 and distal end 54 and includes a concave top surface 59. Secure connection of stud 11 to connector 10 is accomplished by inserting stud 11 into socket 16 such that each of fingers 35 engage stud 11 and flex radially outward. Flexing fingers 35 allows proximal end 58 to be inserted into socket 16, whereupon fingers 35 engage intermediate portion 56 in a secure arrangement.

Now referring to FIG. 2, conductive stud 11 is fully inserted into socket 16 such that each finger 35 electrically and mechanically engages intermediate portion 56 of stud 11 at several contact areas 60. Curved edge 36 tangentially engages annular collar 52 proximate distal end 54 of stud 11 at second contact area 62 to provide a solid electrical and mechanical connection. During insertion of stud 11, when fingers 35 flex outward rim 32 resides within conforming recess 40 and is flush with wall 18. The spring retention of each finger 35 against narrowed intermediate portion 56 of stud 11 ensures a good mechanical and electrical contact at both first contact region 60 and second contact region 62 in a locking manner. Edges of fingers 35 engage or "bite" stud 11 providing a more secure contact than just a single tangent contact between two surfaces. This biting action of each finger 35 cuts through any impurity that may be present on stud 11 or on fingers 35. The spring tension can be designed to meet the desired specifications. A large spring tension can be provided in one or more ways, such as by reducing the diameter defined by the edges of fingers 35, extending the length of fingers 35, providing thicker fingers 35, and selecting a less resilient material. Similarly, a reduced spring tension can be provided by the converse of the listed design techniques.

Circular stud 11 is symmetrically formed and concentrically received within circular socket 16 such that stud 11 is fully rotatable 360° within socket 16 while maintaining physical contacts at regions 60 and 62. Even if connector 10 is urged away from stud 11, such as in accidental tugging by a patient, at least one physical contact between conductive finger 35 and stud 11 is always maintained at contact region 60. Thus, continuous electrical monitoring of the patient at stud 11 is maintained and uninterrupted.

It is particularly noted that a surface of annular rim 32 is not simply in flush contact with curved distal end 54 of stud 11. Hence, a more concentrated force can be maintained against stud 11 by both fingers 35 and edge 36 at regions 60 and 62, respectively, to maintain firm mechanical and electrical contacts. If connector 10 is pressed upon while connected to stud 11, annular surface 26 and edge 36 engage even a greater surface area of flexible annular collar 52, once again maintaining a firm electrical and physical contact.

Referring to FIG. 3, a top view of socket 16 is shown illustrating several radial slits 34 defining fingers 35. Socket 16, rim 32, surface 26 and surface 28 are all concentric forming a symmetrical connector. The symmetry provides easy connection to stud 11 and selectable rotation while maintaining a good electrical and mechanical contact. The several contact fingers 35 provide redundancy of a physical connection between pad 20 and stud 11 should one finger fail or suffer wear and damage. Thus, a failure of a connection between pad 20 and stud 11 is substantially reduced with this improved connector assembly.

Connector 10 is easily manufactured by first crimping finger 22 to conductor 19, which can be done quickly using automated equipment. Next, a mandrel is inserted into the opening in pad 20 to flex fingers 35 radially outward. The mandrel has a separate finger protruding between each finger 35 to create a void radially inward. Connector body 12 is formed by plastic injection molding about pad 20 to complete the assembly of connector 10. When the mandrel is subsequently removed, fingers 35 again flex inward within conforming recess 40 due to biasing properties of fingers 35.

In summary, an improved connector having several flexible contact fingers provides an improved contact area. The connector can be quickly manufactured using automated equipment for crimping and plastic molding injection. The connection between the electrode and the conductor is mechanically secure providing a reliable electrical connection.

This invention has been described herein in considerable detail in order to comply with the Patent Statutes and to provide those skilled in the art with the information needed to apply the novel principles and to construct and use such specialized components as are required. However, it is to be understood that the invention ca be carried out by specifically different equipment and devices, and that various modifications, both as to the equipment details and operating procedures, can be accomplished without departing from the scope of the invention itself.

What is claimed is:

1. In combination, a medical electrical connector and a conductive stud extending out from a patient engaging electrode for establishing an electrical connection between the electrode and connector, the stud having a proximal portion, a distal portion adjacent the electrode and an intermediate portion therebetween, the intermediate portion having a smaller diameter than the diameter of the proximal portion, said proximal portion curving to an annular collar about a base of said stud; The connector comprising:

an insulated conductor;

insulation means for receiving said stud forming a connector body, and shaped to form a socket having an opening defining a socket wall;

a plate-like conductive pad disposed in said insulation means and coupled to said conductor, said conductive pad having an aperture defining an annular contact region and a rim, said rim having several notches defining several rim fingers, wherein a portion of said rim is spaced from said socket wall such that upon inserting said stud in said socket said rim fingers flex radially outward and engage said stud at a first contact area and said annular contact region engages said collar of said stud at a second contact area.

2. The medical electrical connector as specified in claim 1 wherein said socket wall further includes an annular recess proximate said rim fingers, wherein said rim fingers radially flex within said recess when said stud is inserted into said socket.

3. The medical electrical connector as specified in claim 2 wherein said recess closely conforms to radially flexed said rim fingers.

4. The medical electrical connector as specified in claim 1 wherein said rim fingers define a generally frusto-conical shape tapering at least partially into said socket.

5. The medical electrical connector as specified in claim 1 wherein said conductive pad further includes an integrally formed connecting means within said insulation means for connecting to said conductor.

6. The medical electrical connector as specified in claim 5 wherein said connecting means comprises a crimp finger which can be crimped to said conductor.

7. The medical electrical connector as specified in claim 1 wherein said rim fingers engage said intermediate portion of said stud when said stud is inserted in said socket in a locking relationship.

8. The medical electrical connector as specified in claim 1 wherein said notches are defined by radial slits.

* * * * *